(12) United States Patent
Morii et al.

(10) Patent No.: US 11,827,585 B2
(45) Date of Patent: Nov. 28, 2023

(54) METHOD FOR PRODUCING ACRYLONITRILE

(71) Applicant: ASAHI KASEI KABUSHIKI KAISHA, Tokyo (JP)

(72) Inventors: Kazunari Morii, Tokyo (JP); Akiyoshi Fukuzawa, Tokyo (JP)

(73) Assignee: ASAHI KASEI KABUSHIKI KAISHA, Tokyo (JP)

(*) Notice: Subject to any disclaimer, the term of this patent is extended or adjusted under 35 U.S.C. 154(b) by 645 days.

(21) Appl. No.: 17/041,264

(22) PCT Filed: Feb. 19, 2019

(86) PCT No.: PCT/JP2019/005966
§ 371 (c)(1),
(2) Date: Sep. 24, 2020

(87) PCT Pub. No.: WO2019/187786
PCT Pub. Date: Oct. 3, 2019

(65) Prior Publication Data
US 2021/0070693 A1    Mar. 11, 2021

(30) Foreign Application Priority Data

Mar. 28, 2018   (JP) ................................ 2018-061633

(51) Int. Cl.
| | | |
|---|---|---|
| C07C 253/26 | (2006.01) | |
| B01J 8/22 | (2006.01) | |
| B01J 8/24 | (2006.01) | |
| B01J 21/18 | (2006.01) | |
| B01J 23/887 | (2006.01) | |
| B01J 37/16 | (2006.01) | |
| C07C 255/08 | (2006.01) | |

(52) U.S. Cl.
CPC .............. *C07C 253/26* (2013.01); *B01J 8/22* (2013.01); *B01J 8/24* (2013.01); *B01J 21/18* (2013.01); *B01J 23/8876* (2013.01); *B01J 37/16* (2013.01); *B01J 2208/00017* (2013.01); *C07C 255/08* (2013.01)

(58) Field of Classification Search
CPC .................................................. C07C 253/26
See application file for complete search history.

(56) References Cited

U.S. PATENT DOCUMENTS

| | | |
|---|---|---|
| 4,541,964 A | 9/1985 | Katsumata et al. |
| 5,780,664 A | 7/1998 | Aoki |
| 6,653,496 B1 | 11/2003 | Mori et al. |
| 2015/0065744 A1 | 3/2015 | Watanabe et al. |
| 2018/0318803 A1* | 11/2018 | Fukuzawa ............. C07C 253/26 |
| 2019/0001309 A1* | 1/2019 | Fukuzawa ............ B01J 37/0221 |

FOREIGN PATENT DOCUMENTS

| | | | |
|---|---|---|---|
| CN | 1379757 A | 11/2002 | |
| CN | 104144910 A | 11/2014 | |
| JP | 49-20114 A | 2/1974 | |
| JP | 58-72550 A | 4/1983 | |
| JP | 7-51570 A | 2/1995 | |
| JP | 2003-64041 A | 3/2003 | |
| JP | 2003-64042 A | 3/2003 | |
| JP | 2003-64043 A | 3/2003 | |
| JP | 2009-285581 A | 12/2009 | |
| JP | 2010-172851 A | 8/2010 | |
| JP | 2012-67047 A | 4/2012 | |
| JP | 2015-157241 A | 9/2015 | |
| JP | 2015157241 * | 9/2015 | ........... C07C 253/26 |
| JP | 2015-188802 A | 11/2015 | |
| WO | WO 2011/090131 A1 | 7/2011 | |
| WO | WO 2017/130906 A1 | 8/2017 | |
| WO | WO 2017/130909 A1 | 8/2017 | |

OTHER PUBLICATIONS

Extended European Search Report for European Application No. 19776567.0, dated Apr. 12, 2021.
Wu et al., "Reduction/reoxidation of a multicomponent molybdate catalyst for propylene ammoxidation," Thermochimica Acta, vol. 486, No. 1-2, Mar. 20, 2009, pp. 20-26, XP025958550.
English translation of International Preliminary Report on Patentability and Written Opinion dated Oct. 8, 2020, in PCT/JP2019/005966 (Forms PCT/IB/326, PCT/IB/373, and PCT/ISA/237).
English translation of International Search Report dated Apr. 16, 2019, in PCT/JP2019/005966.
International Search Report, issued in PCT/JP2019/005966, PCT/ISA/210, dated Apr. 16, 2019.
Written Opinion of the International Searching Authority, issued in PCT/JP2019/005966, PCT/ISA/237, dated Apr. 16, 2019.

* cited by examiner

*Primary Examiner* — Paul V Ward

(74) *Attorney, Agent, or Firm* — Birch, Stewart, Kolasch & Birch, LLP

(57) ABSTRACT

A method for producing acrylonitrile, having: a catalyst treatment step of preparing a composite metal oxide catalyst including molybdenum, bismuth, and iron and including 50 ppm or more of carbon; and a vapor-phase catalytic oxidation step of subjecting propylene to ammoxidation reaction using the composite metal oxide catalyst to produce acrylonitrile.

7 Claims, 1 Drawing Sheet

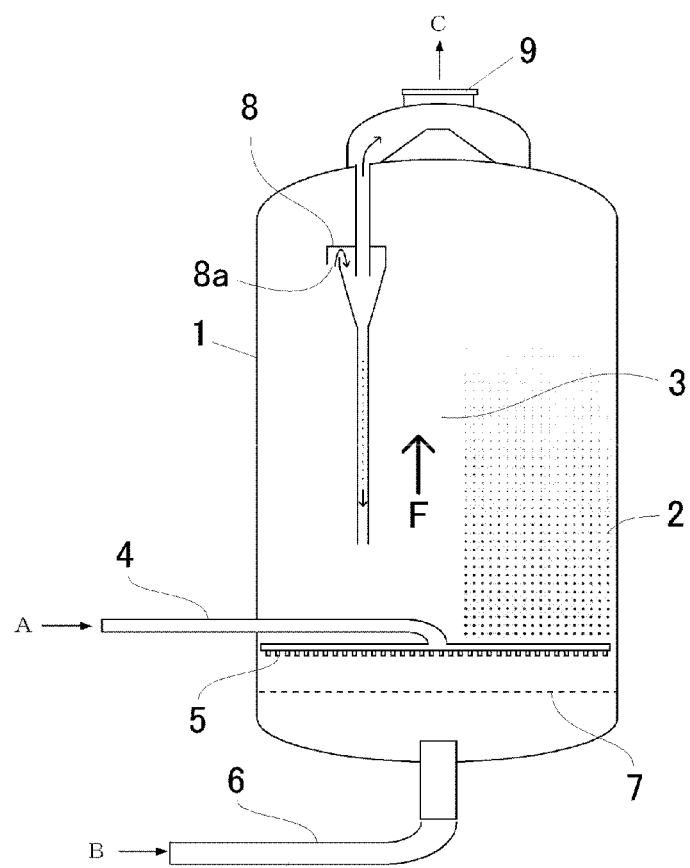

METHOD FOR PRODUCING ACRYLONITRILE

TECHNICAL FIELD

The present invention relates to a method for producing acrylonitrile.

BACKGROUND ART

Conventionally, fluidized bed reactors have been widely used when an alkane and/or alkene is subjected to vapor-phase catalytic ammoxidation reaction in the presence of a composite metal oxide catalyst. Fluidized bed reactors used on an industrial scale are required to operate production in good yields while maintaining safety. From the viewpoint of safety, an oxygen concentration at an discharge port of a fluidized bed reactor is decreased to the flammability limit or less, ammonia is moderately burnt as a means for that, and control of reaction temperature and control of supply amounts of starting materials are conducted. Meanwhile, from the viewpoints of selectivity and yields, control is conducted so that acrylonitrile, synthesized along with combustion of ammonia, does not burn, and deterioration in catalytic performance, which is caused by excessively decreasing the oxygen concentration and exposing the catalyst to a reducing environment thereby, is suppressed. These kinds of control have been studied from the viewpoint of development of catalysts and from the viewpoint of improvement of production methods, respectively.

For example, Patent Literature 1 discloses an oxide catalyst containing molybdenum, bismuth, iron, cobalt, and a lanthanoid element A at a predetermined ratio and including a disorder phase of a catalyst system, which includes molybdenum, bismuth, iron, cobalt, and the lanthanoid element of these elements, at a predetermined amount to provide an oxide catalyst which achieves both an appropriate ammonia combustion rate and a high acrylonitrile yield in acrylonitrile production using propylene as a starting material and to provide a method for producing the oxide catalyst.

CITATION LIST

Patent Literature

Patent Literature 1: Japanese Patent Laid-Open No. 2015-188802

SUMMARY OF INVENTION

Technical Problem

As disclosed in Patent Literature 1, high acrylonitrile selectivity can be obtained by using a specific catalyst. However, the present inventors have further proceeded with investigation and found that selectivity deteriorates over time even using a catalyst having good characteristics. The present inventors have further studied the cause thereof and found that impurities and an organic substance resulting from a byproduct gradually attach to a catalyst during reaction, causing deterioration in catalytic activity and deterioration in the selectivity.

The present invention has been made in view of the above-described problem and aims at providing a method for producing acrylonitrile which is economical because an amount of $NH_3$ used is small and which can suppress chronological deterioration in acrylonitrile selectivity.

Solution to Problem

The present inventors have made intensive studies for solving the above-described problem. As a result, the present inventors have found that the above-described problem may be solved by adjusting an amount of carbon contained in a composite metal oxide catalyst in a vapor-phase catalytic oxidation step, and the present invention has been completed thereby.

That is, the present invention is as follows.

[1]

A method for producing acrylonitrile, comprising:

a catalyst treatment step of preparing a composite metal oxide catalyst comprising molybdenum, bismuth, and iron and comprising 50 ppm or more of carbon; and a vapor-phase catalytic oxidation step of subjecting propylene to ammoxidation reaction using the composite metal oxide catalyst to produce the acrylonitrile.

[2]

The method for producing the acrylonitrile according to [1], wherein the catalyst treatment step has: a pre-step of treating a composite metal oxide comprising molybdenum, bismuth, and iron under a reducing gas and oxygen atmosphere for 50 hours or longer; and a post-step of circulating the composite metal oxide in a hopper with nitrogen or air.

[3]

The method for producing the acrylonitrile according to [1] or [2], wherein the composite metal oxide catalyst prepared in the catalyst treatment step comprises 5000 ppm or less of carbon.

[4]

The method for producing the acrylonitrile according to any one of [1] to [3], wherein a calorific value of an exothermic peak having a peak top at 600° C. or higher in a DTA analysis is 80 J/g or less in the composite metal oxide catalyst prepared in the catalyst treatment step.

[5]

The method for producing the acrylonitrile according to any one of [1] to [4], wherein the carbon comprised in the composite metal oxide catalyst in the vapor-phase catalytic oxidation step is 5000 ppm or less.

[6]

The method for producing the acrylonitrile according to any one of [1] to [5], wherein an oxygen concentration at an discharge port of a fluidized bed reactor in the vapor-phase catalytic oxidation step is 0.2 to 1.0% by volume.

[7]

The method for producing the acrylonitrile according to any one of [1] to [6], wherein a supply amount of starting material per unit catalyst amount (T-Py/T-Cat/hr) in the vapor-phase catalytic oxidation step is 0.08 to 0.11.

[8]

The method for producing the acrylonitrile according to any one of [1] to [7], comprising, before the vapor-phase catalytic oxidation step, a startup step of supplying oxygen to the fluidized bed reactor in which the composite metal oxide catalyst exists and increasing a temperature inside the fluidized bed reactor to 300° C. to 500° C.

Advantageous Effects of Invention

The method for producing acrylonitrile according to the present invention is economical, since an amount of $NH_3$ used is small. In addition, activity is stable from an early stage of reaction, and a method for producing acrylonitrile which can suppress deterioration in acrylonitrile selectivity can be provided.

BRIEF DESCRIPTION OF DRAWINGS

FIG. 1 shows a schematic cross-sectional view of a fluidized bed reactor which may be used in a method for producing acrylonitrile according to an embodiment of the present invention.

DESCRIPTION OF EMBODIMENTS

Hereinafter, an embodiment of the present invention (hereinafter, referred to as "the present embodiment") will be described in detail. However, the present invention is not limited thereto, and various modifications can be made without departing from its spirit. In the FIGURE, the same element is designated by the same sign, and overlapped description will be omitted. In addition, positional relationships such as top and bottom and left and right are based on the positional relationships shown in the FIGURE unless otherwise stated. Furthermore, dimension ratios in the FIGURE are not limited to the illustrated ratios.

[Method for Producing Acrylonitrile]

A method for producing acrylonitrile according to the present embodiment includes a catalyst treatment step of preparing a composite metal oxide catalyst including molybdenum, bismuth, and iron and including 50 ppm or more of carbon; and a vapor-phase catalytic oxidation step of subjecting propylene to ammoxidation reaction using the composite metal oxide catalyst to produce acrylonitrile.

In a fluidized bed reactor continuously operated over a long time, an impurity originating from starting material gas and a reaction byproduct may attach to and precipitate on a surface of a catalyst over time. The impurity and byproduct prevent starting material gas from contacting the catalyst and deteriorate activity of the catalyst, causing chronological deterioration in acrylonitrile selectivity.

On the other hand, in the present embodiment, an amount of $NH_3$ used is reduced and chronological deterioration in acrylonitrile selectivity is suppressed by setting an amount of carbon contained in a catalyst to fall within a predetermined range, and characteristics of the catalyst can be sufficiently exerted throughout long-term operation accordingly.

Hereinafter, a method for producing acrylonitrile according to the present embodiment will be described in detail. A schematic cross-sectional view of a fluidized bed reactor 1 which may be used in the method for producing acrylonitrile according to the present embodiment is firstly shown in FIG. 1.

A catalyst 2 flows in an internal space 3 under its own weight and volume of the catalyst and under a balance among a supply amount of starting material gas A including propylene and ammonia supplied from a dispersion tube 5 via a starting material feed pipe 4, a supply amount of oxygen-containing gas B supplied from a dispersion plate 7 via an oxygen-containing gas feed pipe 6, and the like. An existing amount per unit space (distribution) of the catalyst 2 in the internal space 3 tends to decrease toward an upper side of the internal space 3 from a lower side of the internal space 3 (in the direction of an arrow F) in a region above a dispersion tube 8.

Vapor-phase catalytic oxidation reaction occurs in the internal space 3. Propylene, oxygen, and ammonia are supplied to the flowing catalyst 2 in the internal space 3 to synthesize acrylonitrile, and reaction product gas including acrylonitrile is discharged from an discharge port 9 via a cyclone 8.

A cooling coil (not shown) for removing heat of reaction mainly in a concentrated zone of the internal space 3 to control reaction temperature and a member (not shown) for adjusting gas superficial velocity in the internal space 3 may be provided in the internal space 3 as needed in addition to the cyclone 8 which separates and recovers the catalyst 2 form the reaction product gas C including acrylonitrile. The gas superficial velocity in the internal space 3 varies depending on a cross-sectional area (an area spreading in the direction perpendicular to the direction of the arrow F) of the internal space 3. For example, when an internal space 3 having an un-uniform cross-sectional area is assumed, the gas superficial velocity decreases at a position having a wide cross-sectional area, and the gas superficial velocity increases at a position having a narrow cross-sectional area.

The reaction product gas C accompanied by the catalyst 2 enters the cyclone 8 from an feed port 8a. The catalyst 2 having entered the cyclone 8 falls downward in the internal space 3 while drawing a spiral at a conical part of the cyclone 8, and the reaction product gas is led to an discharge port 9 through a pipe extending upward from an upper part of the cyclone 8. Further, a pipe extends downward in the internal space 3 from a lower part of the conical part of the cyclone 8, and the catalyst 2 passes through the inside of this pipe and is led to the lower part of the internal space 3.

The method for producing acrylonitrile according to the present embodiment is not particularly limited as long as it has the vapor-phase catalytic oxidation step described above but has a catalyst treatment step of treating the catalyst under a predetermined condition before reaction; a catalyst filling step of filling the fluidized bed reactor with the catalyst; a startup step of supplying oxygen to the fluidized bed reactor, in which a composite metal oxide catalyst exists, and increasing the temperature inside the fluidized bed reactor to 300° C. to 500° C., before the vapor-phase catalytic oxidation step; a keeping step of keeping a state where the temperature inside the fluidized bed reactor is increased for 2 to 500 hours after the startup step; and a vapor-phase catalytic oxidation step of supplying ammonia and propylene and causing ammoxidation reaction to synthesize acrylonitrile, for example. Hereinafter, each step will be described in detail.

[Catalyst Treatment Step]

The catalyst treatment step is a step of preparing a composite metal oxide catalyst including molybdenum, bismuth, and iron and including carbon. An amount of carbon in the composite metal oxide catalyst is 50 ppm or more and preferably 50 to 5000 ppm. When the amount of carbon in the composite metal oxide catalyst falls within the above range, an amount of $NH_3$ used can be reduced, and deterioration in acrylonitrile selectivity can be suppressed.

The catalyst treatment step preferably has: a pre-step of treating a composite metal oxide under a reducing gas and oxygen atmosphere for 50 hours or longer, the composite metal oxide being obtained by a usual method; and a subsequent post-step of circulating the composite metal oxide in a hopper with nitrogen or air. By virtue of circulation with nitrogen or air after pre-treatment in this manner, polymerization of carbon included in the composite metal oxide and increase in temperature thereof can be prevented. Carbon with an increased temperature gets difficult to burn during reaction, and attachment of carbon is further caused by carbon with an increased temperature as a seed.

While the reducing gas used in the pre-step is not particularly limited, examples thereof include ammonia. A treatment temperature in the pre-step is preferably 300° C. to 500° C., more preferably 325° C. to 475° C., and still more preferably 350° C. to 450° C. When the treatment temperature falls within the above range, organic substances included in the catalyst at this time point can be burnt to reduce the amount of carbon, and as a result, acrylonitrile selectivity tends to further improve. The pre-step can be conducted using a fluidized bed reactor.

In the post-step, the composite metal oxide is preferably cooled while circulating the composite metal oxide in the hopper with nitrogen or air. A temperature of the composite metal oxide after being cooled is preferably 10° C. to 50° C., more preferably 15° C. to 45° C., and still more preferably 20° C. to 40° C.

Furthermore, in a case where the composite metal oxide catalyst having been already used in the vapor-phase catalytic oxidation step is once taken out and further used in the vapor-phase catalytic oxidation step and when the amount of carbon in the composite metal oxide catalyst is 50 ppm or more, the composite metal oxide catalyst can be regarded as a composite metal oxide catalyst having been subjected to the catalyst treatment step.

Carbon with an increased temperature shows an exothermic peak at 600° C. or higher in its DTA analysis. As described above, carbon with an increased temperature is not desirable, because it gets difficult to burn during reaction, and attachment of carbon is further caused by carbon with an increased temperature as a seed. Form such a viewpoint, a calorific value of an exothermic peak having a peak top at 600° C. or higher is preferably 80 J/g or less and more preferably 50 J/g or less.

[Catalyst Filling Step]

The catalyst filing step is a step of filling the fluidized bed reactor with a catalyst. The inside of the fluidized bed reactor before being filled with the catalyst may be heated or may not be heated but is preferably in a heated state. A temperature inside the fluidized bed reactor before being filled with the catalyst is preferably 125° C. to 275° C., more preferably 150° C. to 250° C., and still more preferably 175° C. to 225° C. When the temperature inside the fluidized bed reactor before being filled with the catalyst is 125° C. or higher, the temperature can be promptly start to rise after the filling of the catalyst, and a fluidized state of the catalyst tends to be good. When the temperature inside the fluidized bed reactor before being filled with the catalyst is 275° C. or lower, a cost per unit time of fuel used to heat gas introduced into the fluidized bed reactor during filling of the catalyst can be kept low.

While the catalyst which may be used in the present embodiment is not particularly limited as long as it is a composite metal oxide catalyst including molybdenum, bismuth, and iron, examples thereof include a metal oxide catalyst carried by silica or the like.

Examples of such a catalyst include a catalyst having a composition represented by following formula (1) but are not particularly limited thereto. Acrylonitrile selectivity tends to further improve by virtue of using such a catalyst.

$$Mo_{12}Bi_aFe_bX_cY_dZ_eO_f \quad (1)$$

(In formula (1), X represents one or more elements selected from the group consisting of nickel, cobalt, magnesium, calcium, zinc, strontium, and barium; Y represents one or more elements selected from the group consisting of cerium, chromium, lanthanum, neodymium, yttrium, praseodymium, samarium, aluminum, gallium, and indium; Z represents one or more elements selected from the group consisting of potassium, rubidium, and cesium; a, b, c, d, and e satisfy $0.1 \leq a \leq 2.0$, $0.1 \leq b \leq 3.0$, $0.1 \leq c \leq 10.0$, $0.1 \leq d \leq 3.0$, and $0.01 \leq e \leq 2.0$, respectively; and f is the number of oxygen atoms required to satisfy valence requirements of other existing elements.)

X is one or more elements selected from the group consisting of nickel, cobalt, magnesium, calcium, zinc, strontium, and barium. Among them, nickel and cobalt are preferable, and nickel and cobalt are preferably used in combination.

Y is one or more elements selected from the group consisting of cerium, chromium, lanthanum, neodymium, yttrium, praseodymium, samarium, aluminum, gallium, and indium, and cerium is preferable among them.

Z is one or more elements selected from the group consisting of potassium, rubidium, and cesium. Potassium and rubidium are preferable, and potassium and rubidium are preferably used in combination.

The subscript a is an atomic ratio of Bi based on 12 molybdenum atoms and is 0.1 to 2.0, preferably 0.1 to 1.5, more preferably 0.2 to 1.2, and still more preferably 0.3 to 0.7.

The subscript b is an atomic ratio of Fe based on 12 molybdenum atoms and is 0.1 to 3.0, preferably 0.5 to 2.5, more preferably 0.8 to 2.2, and still more preferably 1.3 to 2.0.

The subscript c is an atomic ratio of X based on 12 molybdenum atoms and is 0.1 to 10.0, preferably 5.0 to 10.0, more preferably 6.0 to 9.0, and still more preferably 7.0 to 9.0. When two or more elements are used in combination as X, c represents a ratio of the total number of atoms of these elements based on 12 molybdenum atoms.

The subscript d is an atomic ratio of Y based on 12 molybdenum atoms and is 0.1 to 3.0, preferably 0.3 to 2.5, more preferably 0.5 to 2.0, and still more preferably 0.5 to 1.5. When two or more elements are used in combination as Y, d represents a ratio of the total number of atoms of these elements based on 12 molybdenum atoms.

The subscript e is an atomic ratio of Z based on 12 molybdenum atoms and is 0.01 to 2.0, preferably 0.1 to 1.5, more preferably 0.1 to 1.0, and still more preferably 0.1 to 0.7. When two or more elements are used in combination as Z, e represents a ratio of the total number of atoms of these elements based on 12 molybdenum atoms.

An average particle diameter of the catalyst is preferably 20 to 100 μm, more preferably 30 to 90 μm, and still more preferably 40 to 80 μm. A particle diameter range (a range including a minimum particle diameter and a maximum particle diameter) of the catalyst is preferably 1 to 500 μm, more preferably 5 to 400 μm, and still more preferably 10 to 250 μm. When the average particle diameter and the particle diameter range fall within the above ranges, acrylonitrile selectivity tends to further improve.

The catalyst of the present embodiment may be a catalyst in which a composite metal oxide having the above composition is carried by a carrier. While the carrier is not particularly limited as long as it is generally used as a catalyst carrier, examples thereof include silica, alumina, titania, and zirconia. Among them, silica is preferable from the view point that wear resistance of catalyst particles and particle strength become good. An amount of the carrier is preferably 20% to 70% by mass, more preferably 30% to 60% by mass, and still more preferably 30% to 50% by mass based on the total mass of the catalyst (composite metal oxide) and the carrier.

While a method for producing the catalyst is not particularly limited, examples thereof include a method including a mixing step of mixing starting materials including respective atoms constituting the catalyst with a chelating agent as needed to obtain starting material slurry; drying step of drying the obtained starting material slurry to obtain a dried body; and calcining the obtained dried body. Calcination may be conducted in multiple stages.

[Startup Step]

The startup step is a step of supplying oxygen into the fluidized bed reactor in which the composite metal oxide catalyst exists before the vapor-phase catalytic oxidation step and increasing the temperature inside the fluidized bed reactor to 300° C. to 500° C. A method of supplying oxygen is not particularly limited, but oxygen can be supplied from the dispersion plate 7 via the oxygen-containing gas feed pipe 6. Oxygen may be supplied together with inert gas such as nitrogen or argon, respectively.

The temperature inside the fluidized bed reactor in the present embodiment herein refers to a temperature in the internal space 3 and can be measured as an average value of temperatures at the 20th to 24th divisions from the bottom when a height (distance in the flowing direction) of the fluidized bed reactor is divided into 100 hundredths. An increased temperature inside the fluidized bed reactor in the startup step is preferably 300° C. to 500° C., more preferably 325° C. to 475° C., and still more preferably 350° C. to 450° C. When the increased temperature inside the reactor falls within the above range, organic substances included in the catalyst at this time point can be burnt to reduce the amount of carbon, and as a result, acrylonitrile selectivity tends to further improve.

[Keeping Step]

The keeping step is a step of keeping a state where the temperature inside the fluidized bed reactor is increased for 2 to 500 hours after the startup step. While a method for keeping the state where the temperature inside the fluidized bed reactor is increased is not particularly limited, examples thereof include a method of continuously supplying heated air. By virtue of having the keeping step, organic substances included in the catalyst at this time point can be burnt to reduce the amount of carbon, and as a result, acrylonitrile selectivity tends to further improve.

A keeping time in the keeping step is preferably 2 to 20 hours, more preferably 3 to 16 hours, and still more preferably 4 to 12 hours. When the keeping time in the keeping step is two hours or longer, organic substances included in the catalyst can be burnt to reduce the amount of carbon, and as a result, acrylonitrile selectivity tends to further improve. When the keeping time in the keeping step is 20 hours or shorter, a time required for the keeping step can be shortened, and a cost of fuel can be kept low.

The temperature inside the fluidized bed reactor in the keeping step can be the same temperature as in the startup step and is preferably 300° C. to 500° C., more preferably 325° C. to 475° C., and still more preferably 350° C. to 450° C.

[Vapor-Phase Catalytic Oxidation Step]

The vapor-phase catalytic oxidation step is a step of subjecting propylene to ammoxidation reaction using the composite metal oxide catalyst having been subjected to the catalyst treatment step described above to produce acrylonitrile. Specifically, when the startup step or the startup step followed by the keeping step is conducted, the vapor-phase catalytic oxidation step is started by supplying ammonia and propylene to the fluidized bed reactor after the startup step or the keeping step until supply amounts thereof fall within target ranges. On starting the vapor-phase catalytic oxidation step, ammonia and propylene may be simultaneously supplied, or ammonia and propylene may be supplied in stages such that one of ammonia and propylene may be firstly supplied to reach a predetermined supply amount, and the other one may be subsequently supplied to reach a predetermined supply amount.

In the vapor-phase catalytic oxidation step, an amount of carbon included in the composite metal oxide catalyst is preferably 5000 ppm or less. While a method for keeping the amount of carbon small is not particularly limited, examples thereof include a method of adjusting a supply amount of oxygen, a method of adjusting a supply amount of starting material per unit catalyst amount (T-Py/T-Cat), and a method of conducting the startup step and/or the startup step followed by the keeping step described above.

The amount of carbon included in the composite metal oxide catalyst in the vapor-phase catalytic oxidation step is 50 ppm or more and more preferably 100 ppm or more. When the amount of carbon attaching to the catalyst is 50 ppm or more, extra $NH_3$ decomposition active sites in the catalyst are blocked, and an amount of $NH_3$ used can be reduced. An upper limit of the amount of carbon included in the composite metal oxide catalyst is 5000 ppm or less, preferably 4500 ppm or less, more preferably 4000 ppm or less, and still more preferably 3000 ppm or less. The amount of carbon included in the composite metal oxide catalyst is a total amount of an amount of carbon existing on a surface of the composite metal oxide catalyst and an amount of carbon existing inside thereof and specifically a value measured by the method described in Examples.

Examples of a method for adjusting the supply amount of oxygen include a method of monitoring an oxygen concentration at the discharge port of the reactor as a rough indication and conducting operation so that the oxygen concentration at the discharge port of the reactor falls within a predetermined range from the viewpoint of keeping the amount of carbon small. In the vapor-phase catalytic oxidation step, the oxygen concentration at the discharge port of the fluidized bed reactor is preferably 0.2% to 1.0% by volume, more preferably 0.3% to 1.0% by volume, and still more preferably 0.4% to 0.9% by volume. When the oxygen concentration at the discharge port in the vapor-phase catalytic oxidation step is 0.2% by volume or more, carbon included in the composite metal oxide catalyst easily burns, and the amount of carbon tends to decrease. When the oxygen concentration at the discharge port in the vapor-phase catalytic oxidation step is 1.0% by volume or less, explosion under an oxygen-rich atmosphere tends to be suppressed. The oxygen concentration at the discharge port can be controlled by adjusting an oxygen amount to be supplied.

The supply amount of starting material per unit catalyst amount (T-Py/T-Cat/hr) is preferably 0.08 to 0.11, more preferably 0.085 to 0.11, and still more preferably 0.09 to 0.105 from the viewpoint of keeping the amount of carbon small. When the supply amount of starting material per unit catalyst amount (T-Py/T-Cat/hr) is 0.08 or more, flowability of the catalyst in the fluidized bed reactor improves, and the amount of carbon included in the composite metal oxide catalyst tends to decrease. When the supply amount of starting material per unit catalyst amount (T-Py/T-Cat/hr) is 0.11 or less, reactivity tends to further improve. T-Py means a supply amount of propylene supplied per unit hour (Nm$^3$/hr), and T-Cat means a catalyst amount (T) existing in the fluidized bed reactor. In order to adjust the supply amount of starting material per unit catalyst amount (T-Py/T-Cat/hr) to fall within the above range, values of its numerator T-Py and denominator T-Cat may be respectively adjusted to adjust the ratio thereof to fall within the above range. Examples of specific operation thereof include a method of adding a fresh catalyst with time to the fluidized bed reactor and a method of removing a part of the catalyst in the fluidized bed reactor in addition to addition of a catalyst. (that is, a method in which a part of the catalyst in the fluidized bed reactor is replaced with a fresh catalyst).

The supply amount of starting material per unit catalyst amount (T-Py/T-Cat/hr) is calculated according to the following equation.

T-Py/T-Cat/hr=Py×42.08/22400×1/Wcat

Py: Supply amount of propylene (Nm$^3$/hr)
42.08: Molecular weight of propylene (g/mol)
22400: Volume of 1 mol of gas in standard state (L/mol)
Wcat: Amount of catalyst existing in fluidized bed reactor (T)

A temperature inside the fluidized bed reactor in the vapor-phase catalytic oxidation step is preferably 400° C. to 460° C., more preferably 410° C. to 450° C., and still more preferably 420° C. to 440° C. When the temperature inside the reactor falls within the above range, acrylonitrile selectivity tends to further improve.

A sulfuric acid consumption unit in the vapor-phase catalytic oxidation step is preferably 12.5 to 27.5 kg/T-AN, more preferably 15 to 25 kg/T-AN, and still more preferably 17.5 to 22.5 kg/T-AN. The sulfuric acid consumption unit is an index represented by the following equation and is a value obtained from an amount of acrylonitrile and an amount of unreacted ammonia in reaction product gas according to the following equation. In the present embodiment, by virtue of using a catalyst having a predetermined ammonia combustion rate, acrylonitrile can be obtained in a good yield even at a relatively low temperature. Especially, efficiency of acrylonitrile production tends to further improve by adjusting supply amounts of respective starting materials so that the sulfuric acid consumption unit falls within the above range.

Sulfuric acid consumption unit=(weight of sulfuric acid required to neutralize unreacted ammonia)/(weight of acrylonitrile produced)

A supply amount of ammonia in the vapor-phase catalytic oxidation step is preferably 0.5 to 1.6 moles, more preferably 0.6 to 1.5 moles, and still more preferably 0.7 to 1.4 moles based on one mole of propylene. A supply amount of oxygen in the vapor-phase catalytic oxidation step is preferably 6.0 to 15.5 moles, more preferably 7.0 to 14.5 moles, and still more preferably 8.0 to 13.5 moles based on one mole of propylene. When the supply amount rates of starting materials fall within the above ranges, the amount of carbon tends to be kept small.

[Reaction Stopping Step]

The method for producing acrylonitrile according to the present embodiment may have a reaction stopping step of stopping vapor-phase catalytic oxidation reaction. Stopping of reaction refers to releasing of a steady operation state of the fluidized bed reactor by reducing a supply amount of at least one of propylene, oxygen, and ammonia. Accordingly, a time point at which a supply amount of at least one of propylene, oxygen, and ammonia starts to be reduced for stopping reaction becomes the starting point of the reaction stopping step, and a time point at which vapor-phase catalytic oxidation reaction completely stops becomes the terminal point of the reaction stopping step.

EXAMPLES

Hereinafter, the present invention will be described more specifically using Examples and Comparative Examples. However, the present invention is not limited by the following Examples at all.

A fluidized bed reactor at least having the configuration described in FIG. 1 as a basic configuration was used. Specifically, a fluidized bed reactor which had a vertically cylindrical shape with an inner diameter of 8 m and a length of 25 m, had a dispersion plate 7 for oxygen positioned at two meters from the bottom, and had a dispersion tube 5 for supplying propylene and ammonia above the dispersion plate 7 and which was internally equipped with a heat removal pipe was used. A total of twelve thermometers including eight thermometers provided at a cross-sectional surface positioned at a height of 5 m from the bottom of the reactor (at a part corresponding to the 20th division from the bottom when the height of the fluidized bed reactor was divided into 100 hundredths) and four thermometers provided at a cross-sectional surface positioned at a height of 6 m (at a part corresponding to the 24th division from the bottom when the height of the fluidized bed reactor was divided into 100 hundredths) was provided, and an average value obtained from these thermometers was regarded as the temperature inside the reactor. Reaction product gas flowing out from the discharge port 9 was sampled, and its composition was determined by chromatography.

[Amount of Carbon]

The amount of carbon included in a catalyst was measured using MICRO CORDER JM11 manufactured by J-Science Lab Co., Ltd. Specifically, the fluidized bed reactor was operated under the conditions described in each of the following Examples and Comparative Examples, and each catalyst was sampled from the fluidized bed reactor during operation. Then, measurement was conducted at 950° C. using 100 mg of each sample while supplying helium at 200 mL/minute and oxygen at 15 mL/minute. Antipyrine was used for a standard curve and y=ax was used as a calculation equation.

A calorific value generated from carbon included in a catalyst was measured by using a balance standard model differential thermal TG-DTA (Thermo plus EVO2) manufactured by Rigaku Corporation. Specifically, the fluidized bed reactor was operated under the conditions described in each of the following Examples and Comparative Examples, and each catalyst was sampled from the fluidized bed reactor during operation. Then, measurement was conducted by increasing the temperature from ordinary temperature to 900° C. at a temperature rising rate of 10° C./minute using 80 mg of each sample while supplying O$_2$ at 80 cc/minute.

[Acrylonitrile Selectivity, Ammonia Combustion Rate, Activity, and Rate of Change in Activity]

Acrylonitrile selectivity, an ammonia combustion rate, activity, and a rate of change in activity were calculated according to the following equations after measurement using a fixed bed reaction pipe made of SUS and having an inner diameter of 10ϕ.

[Evaluation on Reaction Performance of Oxide Catalyst]]

Specifically, the fluidized bed reactor was operated under the conditions described in each of the following Examples and Comparative Examples, and each catalyst was sampled from the fluidized bed reactor during operation. Then, measurement was conducted by using 1 mg of each sample at a reaction temperature of 440° C., a total gas amount of 40 cc/min, a propylene supply amount of 5.4 vol %, an ammonia supply amount which was 1.2 moles per one mole of propylene, an oxygen supply amount which was 1.89 moles per one mole of propylene, a water supply amount which was 1.85 moles per one mole of propylene, and a reaction pressure in the course of nature.

Acrylonitrile selectivity (%)=(the number of moles of acrylonitrile produced/the number of moles of propylene reacted)×100

Ammonia combustion rate (%)=(the number of moles of ammonia having burnt to produce nitrogen and water/the number of moles of propylene supplied)×100

Activity (1000/hr)=3.6×LN(100/(100−propylene conversion rate))/contact time (sec)

(In the above equation, LN represents a natural logarithm function.)

Rate of change in activity (%)=((activity before starting reaction−activity after stopping reaction)/activity after stopping reaction)×100

Contact time (sec)=(amount of catalyst (cc)/flow volume of mixed gas (cc))×(273/(273+reaction temperature (° C.)))×(reaction pressure (MPa)/0.10)

Propylene conversion rate (%)=(the number of moles of propylene reacted/the number of moles of propylene supplied)×100

Production Example 1: Molybdenum-Bismuth-Iron-Based Catalyst

A catalyst in which a metal oxide having a bulk composition represented by $Mo_{12.00}Bi_{0.35}Ce_{0.90}Fe_{2.00}Ni_{4.00}Mg_{4.00}Rb_{0.10}O_f$ (in which f was the number of oxygen atoms required to satisfy valence requirements of other elements) was carried by 40% by mass of silica was produced.

Specifically, ammonium heptamolybdate was dissolved in hot water, and ammonia water (28%) was added thereto (liquid A). Besides, bismuth nitrate, iron nitrate, magnesium nitrate, nickel nitrate, cerium nitrate, and rubidium nitrate were dissolved in 16.6% by mass of an aqueous nitric acid solution (liquid B). Liquid A was added to silica sol in which silica serving as a carrier was dispersed, and liquid B was subsequently added thereto followed by stirring and mixing. Thereafter, the resultant starting material slurry was spray dried, and powder obtained after spray drying was calcined to prepare the above-described catalyst. Particle diameters (including carriers) of the obtained catalyst were 10 to 100 μm and an average particle diameter (including carriers) thereof was 55 μm.

Example 1

A fluidized bed reactor the temperature of which was increased to 200° C. by supplying heated air from its dispersion plate was filled with 120 T of the catalyst obtained by Production Example 1. After the completion of filling, the temperature inside the reactor was increased to 400° C. by supplying heated air from a dispersion plate. Thereafter, ammonia and propylene were supplied from the dispersion tube, and treatment was conducted for 50 hr. Thereafter, the catalyst was discharged to a hopper and cooled to room temperature while circulating air (catalyst treatment step). In this case, an amount of attaching carbon was 52 ppm, and no exothermic peak was detected at 600° C. or higher.

A fluidized bed reactor the temperature of which was increased to 200° C. by supplying heated air from its dispersion plate was filled with 120 T of the catalyst obtained through catalyst treatment (catalyst filling step). After the completion of filling, the temperature inside the reactor was increased to 400° C. by supplying heated air from the dispersion plate (startup step), and this state was kept for eight hours (keeping step).

Thereafter, ammonia and propylene were supplied from a dispersion tube to start ammoxidation reaction. At this time, a reaction temperature and a reaction pressure were adjusted to be 430° C. and 0.17 MPa, respectively, and respective supply amounts were adjusted so that the molar ratio of propylene/ammonia/air became 1/(0.7 to 1.4)/(8.0 to 13.5). In addition, an ammonia flow rate was appropriately changed within the above range of molar ratio so that the sulfuric acid consumption unit became 20±3 kg/T-AN. The oxygen concentration in reactor discharge port gas was set to 0.5% by volume, and the supply amount of starting material per unit catalyst amount (T-Py/T-CAT/hr) was set to 0.10. Operation was continuously carried out under this state for 60 days. The acrylonitrile selectivity, $NH_3$ combustion rate, and rate of change in activity in this case were 89.2%, 16%, and 5.1%, respectively.

Example 2

Catalyst treatment was conducted in the same manner as in Example 1 except that the treatment time in the catalyst treatment step was changed to 120 hr. In this case, an amount of attaching carbon was 125 ppm, and no exothermic peak was detected at 600° C. or higher. Operation was continuously carried out as in the case of Example 1 for 60 days using this catalyst. The acrylonitrile selectivity, $NH_3$ combustion rate, and rate of change in activity in this case were 89.0%, 17%, and 4.3%, respectively.

Example 3

Catalyst treatment was conducted in the same manner as in Example 1 except that the treatment time in the catalyst treatment step was changed to 240 hr. In this case, an amount of attaching carbon was 312 ppm, and no exothermic peak was detected at 600° C. or higher. Operation was continuously carried out as in the case of Example 1 for 60 days using this catalyst. The acrylonitrile selectivity, $NH_3$ combustion rate, and rate of change in activity in this case were 88.8%, 18%, and 2.9%, respectively.

Example 4

Catalyst treatment was conducted in the same manner as in Example 1 except that the treatment time in the catalyst treatment step was changed to 480 hr. In this case, an amount of attaching carbon was 550 ppm, and no exothermic peak was detected at 600° C. or higher. Operation was continuously carried out as in the case of Example 1 for 60 days using this catalyst. The acrylonitrile selectivity, $NH_3$ combustion rate, and rate of change in activity in this case were 88.5%, 20%, and 1.1%, respectively.

Example 5

Catalyst treatment was conducted in the same manner as in Example 1 except that the treatment time in the catalyst treatment step was changed to 960 hr. In this case, an amount of attaching carbon was 1420 ppm, and no exothermic peak was detected at 600° C. or higher. Operation was continuously carried out as in the case of Example 1 for 60 days using this catalyst. The acrylonitrile selectivity, $NH_3$ combustion rate, and rate of change in activity in this case were 88.0%, 23%, and 1.0%, respectively.

Example 6

Catalyst treatment was conducted in the same manner as in Example 1 except that the treatment time in the catalyst treatment step was changed to 1920 hr. In this case, an amount of attaching carbon was 3268 ppm, and no exothermic peak was detected at 600° C. or higher. Operation was continuously carried out as in the case of Example 1 for 60 days using this catalyst. The acrylonitrile selectivity, $NH_3$ combustion rate, and rate of change in activity in this case were 87.8%, 27%, and 0.4%, respectively.

Example 7

Catalyst treatment was conducted in the same manner as in Example 1 except that the treatment time in the catalyst treatment step was changed to 480 hr, and the catalyst was cooled to room temperature without circulating air at the time of discharging the catalyst to the hopper. In this case, an amount of attaching carbon was 925 ppm, and a calorific value at 600° C. or higher was 10 J/g. Operation was continuously carried out as in the case of Example 1 for 15 days using this catalyst. The acrylonitrile selectivity, $NH_3$ combustion rate, and rate of change in activity in this case were 87.8%, 22%, and 0.5%, respectively.

Example 8

Catalyst treatment was conducted in the same manner as in Example 7 except that the treatment time in the catalyst treatment step was changed to 960 hr. In this case, an amount of attaching carbon was 2240 ppm, and a calorific value at 600° C. or higher was 33 J/g. Operation was continuously carried out as in the case of Example 1 for 15 days using this catalyst. The acrylonitrile selectivity, $NH_3$ combustion rate, and rate of change in activity in this case were 87.4%, 25%, and 0.3%, respectively.

Example 9

Catalyst treatment was conducted in the same manner as in Example 7 except that the treatment time in the catalyst treatment step was changed to 1920 hr. In this case, an amount of attaching carbon was 4880 ppm, and a calorific value at 600° C. or higher was 78 J/g. Operation was continuously carried out as in the case of Example 1 for 15 days using this catalyst. The acrylonitrile selectivity, $NH_3$ combustion rate, and rate of change in activity in this case were 83.2%, 27%, and 0.5%, respectively.

Example 10

Catalyst treatment was conducted in the same manner as in Example 7 except that the treatment time in the catalyst treatment step was changed to 1980 hr. In this case, an amount of attaching carbon was 5889 ppm, and a calorific value at 600° C. or higher was 87 J/g. Operation was continuously carried out as in the case of Example 1 for 15 days using this catalyst. The acrylonitrile selectivity, $NH_3$ combustion rate, and rate of change in activity in this case were 81.9%, 27%, and 0.4%, respectively.

Example 11

Operation was continuously carried out in the same manner as in Example 1 for 30 days except that the catalyst of Example 1 was used, the oxygen concentration in reactor discharge port gas was set to 1.0% by volume, and the supply amount of starting material per unit catalyst amount (T-Py/T-CAT/hr) was set to 0.10. In this case, an amount of attaching carbon was 55 ppm, and the acrylonitrile selectivity, $NH_3$ combustion rate, and rate of change in activity were 89.2%, 16%, and 5.2%, respectively.

Example 12

Operation was continuously carried out in the same manner as in Example 1 for 30 days except that the catalyst of Example 1 was used, the oxygen concentration in reactor discharge port gas was set to 0.2% by volume, and the supply amount of starting material per unit catalyst amount (T-Py/T-CAT/hr) was set to 0.10. In this case, an amount of attaching carbon was 72 ppm, and the acrylonitrile selectivity, $NH_3$ combustion rate, and rate of change in activity were 89.2%, 16%, and 5.9%, respectively.

Example 13

Operation was continuously carried out in the same manner as in Example 1 for 30 days except that the catalyst of Example 1 was used, the oxygen concentration in reactor discharge port gas was set to 0.1% by volume, and the supply amount of starting material per unit catalyst amount (T-Py/T-CAT/hr) was set to 0.10. In this case, an amount of attaching carbon was 1558 ppm, and the acrylonitrile selectivity, $NH_3$ combustion rate, and rate of change in activity were 88.0%, 20%, and 9.3%, respectively.

Example 14

Operation was continuously carried out in the same manner as in Example 1 for 30 days except that the catalyst of Example 1 was used, the oxygen concentration in reactor discharge port gas was set to 0.5% by volume, and the supply amount of starting material per unit catalyst amount (T-Py/T-CAT/hr) was set to 0.08. In this case, an amount of attaching carbon was 102 ppm, and the acrylonitrile selectivity, $NH_3$ combustion rate, and rate of change in activity were 89.1%, 16%, and 5.8%, respectively.

Example 15

Operation was continuously carried out in the same manner as in Example 1 for 30 days except that the catalyst of Example 1 was used, the oxygen concentration in reactor discharge port gas was set to 0.5% by volume, and the supply amount of starting material per unit catalyst amount (T-Py/T-CAT/hr) was set to 0.07. In this case, an amount of attaching carbon was 1105 ppm, and the acrylonitrile selectivity, $NH_3$ combustion rate, and rate of change in activity were 88.3%, 19%, and 6.8%, respectively.

Example 16

Operation was continuously carried out in the same manner as in Example 1 for 30 days except that the catalyst of Example 1 was used, the oxygen concentration in reactor discharge port gas was set to 0.5% by volume, and the supply amount of starting material per unit catalyst amount (T-Py/T-CAT/hr) was set to 0.11. In this case, an amount of attaching carbon was 58 ppm, and the acrylonitrile selectivity, $NH_3$ combustion rate, and rate of change in activity were 89.2%, 16%, and 6.2%, respectively.

Example 17

Operation was continuously carried out in the same manner as in Example 1 for 30 days except that the catalyst of Example 6 was used, the oxygen concentration in reactor discharge port gas was set to 0.2% by volume, and the supply amount of starting material per unit catalyst amount (T-Py/T-CAT/hr) was set to 0.10. In this case, an amount of attaching carbon was 5990 ppm, and the acrylonitrile selectivity, $NH_3$ combustion rate, and rate of change in activity were 87.1%, 27%, and 0.5%, respectively.

Example 18

Operation was continuously carried out in the same manner as in Example 1 for 30 days except that the catalyst of Example 9 was used, the oxygen concentration in reactor discharge port gas was set to 0.2% by volume, and the supply amount of starting material per unit catalyst amount (T-Py/T-CAT/hr) was set to 0.10. In this case, an amount of attaching carbon was 6449 ppm, and the acrylonitrile selectivity, $NH_3$ combustion rate, and rate of change in activity were 82.8%, 28%, and 0.5%, respectively.

Comparative Example 1

Operation was continuously carried out in the same manner as in Example 1 for 60 days except that no catalyst treatment was conducted.

The acrylonitrile selectivity, $NH_3$ combustion rate, and rate of change in activity in this case were 89.2%, 40%, and 15.3%, respectively.

Comparative Example 2

Catalyst treatment was conducted in the same manner as in Example 1 except that the treatment time in the catalyst treatment step was changed to 15 hr. In this case, an amount of attaching carbon was 20 ppm, and no exothermic heat was detected at 600° C. or higher. Operation was continuously carried out as in the case of Example 1 for 60 days using this catalyst. The acrylonitrile selectivity, $NH_3$ combustion rate, and rate of change in activity in this case were 89.2%, 38%, and 13.1%, respectively.

TABLE 1

| | With respect to catalyst used for reaction | | | | With respect to conditions during reaction | | Analysis results after finishing operation | | | |
|---|---|---|---|---|---|---|---|---|---|---|
| | Catalyst treatment time (hr) | Presence or absence of aeration | Amount of carbon in catalyst used (ppm) | Calorific value at 600° C. or higher (J/g) | Oxygen concentration at discharge port (%) | Amount of catalyst per unit starting material | Operating days (day) | $NH_3$ combustion rate (%) | AN selectivity (%) | Rate of change in activity (%) |
| Example 1 | 50 | Present | 52 | 0 | 0.5 | 0.10 | 60 | 16 | 89.2 | 5.1 |
| Example 2 | 120 | Present | 125 | 0 | 0.5 | 0.10 | 60 | 17 | 89.0 | 4.3 |
| Example 3 | 240 | Present | 312 | 0 | 0.5 | 0.10 | 60 | 18 | 88.8 | 2.9 |
| Example 4 | 480 | Present | 550 | 0 | 0.5 | 0.10 | 60 | 20 | 88.5 | 1.1 |
| Example 5 | 960 | Present | 1420 | 0 | 0.5 | 0.10 | 60 | 23 | 88.0 | 1.0 |
| Example 6 | 1920 | Present | 3268 | 0 | 0.5 | 0.10 | 60 | 27 | 87.8 | 0.4 |
| Example 7 | 480 | Absent | 925 | 10 | 0.5 | 0.10 | 15 | 22 | 87.8 | 0.5 |
| Example 8 | 960 | Absent | 2240 | 33 | 0.5 | 0.10 | 15 | 25 | 87.4 | 0.3 |
| Example 9 | 1920 | Absent | 4880 | 78 | 0.5 | 0.10 | 15 | 27 | 83.2 | 0.5 |
| Example 10 | 1980 | Absent | 5889 | 87 | 0.5 | 0.10 | 15 | 27 | 81.9 | 0.4 |
| Comparative Example 1 | — | — | 0 | 0 | 0.5 | 0.10 | 60 | 40 | 89.2 | 15.3 |
| Comparative Example 2 | 15 | Present | 20 | 0 | 0.5 | 0.10 | 60 | 38 | 89.2 | 13.1 |

TABLE 2

| | With respect to conditions during reaction | | | Analysis results after finishing operation | | | |
|---|---|---|---|---|---|---|---|
| | Oxygen concentration at discharge port (%) | Amount of catalyst per unit starting material | Operating days (day) | Amount of carbon in catalyst after operation (ppm) | $NH_3$ combustion rate (%) | AN selectivity (%) | Rate of change in activity (%) |
| Example 11 | 1.0 | 0.10 | 30 | 55 | 16 | 89.2 | 5.2 |
| Example 12 | 0.2 | 0.10 | 30 | 72 | 16 | 89.2 | 5.9 |
| Example 13 | 0.1 | 0.10 | 30 | 1558 | 20 | 88.0 | 9.3 |
| Example 14 | 0.5 | 0.08 | 30 | 102 | 16 | 89.1 | 5.8 |
| Example 15 | 0.5 | 0.07 | 30 | 1105 | 19 | 88.3 | 6.8 |

TABLE 2-continued

| | With respect to conditions during reaction | | | Analysis results after finishing operation | | | |
|---|---|---|---|---|---|---|---|
| | Oxygen concentration at discharge port (%) | Amount of catalyst per unit starting material | Operating days (day) | Amount of carbon in catalyst after operation (ppm) | NH$_3$ combustion rate (%) | AN selectivity (%) | Rate of change in activity (%) |
| Example 16 | 0.5 | 0.11 | 30 | 58 | 16 | 89.2 | 6.2 |
| Example 17 | 0.2 | 0.10 | 30 | 5990 | 27 | 87.1 | 0.5 |
| Example 18 | 0.2 | 0.10 | 30 | 6449 | 28 | 82.8 | 0.5 |

INDUSTRIAL APPLICABILITY

The present invention has industrial applicability as a method for producing acrylonitrile.

REFERENCE SIGNS LIST

1: fluidized bed reactor
2: catalyst
3: internal space
4: starting material feed pipe
5: dispersion tube
6: oxygen-containing gas feed pipe
7: dispersion plate
8: cyclone
8a: feed port
9: discharge port
A: starring material gas
B: oxygen-containing gas
C: reaction product gas

The invention claimed is:

1. A method for producing acrylonitrile, comprising:
a catalyst treatment step of preparing a composite metal oxide catalyst comprising molybdenum, bismuth, and iron and comprising 50 ppm or more of carbon; and
a vapor-phase catalytic oxidation step of subjecting propylene to ammoxidation reaction using the composite metal oxide catalyst to produce the acrylonitrile,
wherein the catalyst treatment step has:
a pre-step of treating a composite metal oxide comprising molybdenum, bismuth, and iron under a reducing gas and oxygen atmosphere for 50 hours or longer; and
a post-step of circulating the composite metal oxide in a hopper with nitrogen or air.

2. The method for producing the acrylonitrile according to claim 1, wherein
the composite metal oxide catalyst prepared in the catalyst treatment step comprises 5000 ppm or less of carbon.

3. The method for producing the acrylonitrile according to claim 1, wherein
a calorific value of an exothermic peak having a peak top at 600° C. or higher in a DTA analysis is 80 J/g or less in the composite metal oxide catalyst prepared in the catalyst treatment step.

4. The method for producing the acrylonitrile according to claim 1, wherein
the carbon comprised in the composite metal oxide catalyst in the vapor-phase catalytic oxidation step is 5000 ppm or less.

5. The method for producing the acrylonitrile according to claim 1, wherein
an oxygen concentration at a discharge port of a fluidized bed reactor in the vapor-phase catalytic oxidation step is 0.2 to 1.0% by volume.

6. The method for producing the acrylonitrile according to claim 1, wherein
a supply amount of starting material per unit catalyst amount (T-Py/T-Cat/hr) in the vapor-phase catalytic oxidation step is 0.08 to 0.11.

7. The method for producing the acrylonitrile according to claim 1, comprising, before the vapor-phase catalytic oxidation step, a startup step of supplying oxygen to the fluidized bed reactor in which the composite metal oxide catalyst exists and increasing a temperature inside the fluidized bed reactor to 300° C. to 500° C.

* * * * *